United States Patent [19]

Friedman et al.

[11] Patent Number: 5,549,892
[45] Date of Patent: Aug. 27, 1996

[54] ENHANCED IN VIVO UPTAKE OF GLUCOCEREBROSIDASE

[75] Inventors: BethAnn Friedman, Arlington; Michael Hayes, Acton, both of Mass.

[73] Assignee: Genzyme Corporation, Cambridge, Mass.

[21] Appl. No.: 80,855

[22] Filed: Jun. 21, 1993

Related U.S. Application Data

[60] Continuation-in-part of Ser. No. 748,283, Aug. 21, 1991, Pat. No. 5,236,838, which is a division of Ser. No. 455,507, Dec. 22, 1989, abandoned, which is a continuation-in-part of Ser. No. 289,589, Dec. 23, 1988, abandoned.

[51] Int. Cl.$^6$ .................. A61K 38/47; C12N 9/42; C12N 15/56
[52] U.S. Cl. .............. 424/94.61; 435/209; 536/232
[58] Field of Search .................. 424/94.61; 536/23.2; 435/209

[56] References Cited

U.S. PATENT DOCUMENTS 4,713,339  12/1987  Levinson et al. .................. 435/240.2

OTHER PUBLICATIONS

Tsuji, S. et al. (1986) "Nucleotide Sequence of cDNA Containing the Complete Coding Sequence for Human Lysosomal Glucocerebrosidase" *The Journal of Biological Chemistry*, 261(1):50–53.

Sorge, J. et al. (1985) "Molecular Cloning and Nucleotide Sequence of Human Glucocerebrosidase cDNA" *Proc. Natl. Acad. Sci, USA*, 82:7289–7293.

Furbish, F. S. et al (1981) "Uptake and Distribution of Placental Glucocerebrosidase in Rat Hepatic Cells and Effects of Sequential Deglycosylation" *Biochimica et Biophysica Acta*, 673:425–434.

Furbish, F. S. et al. (1977) "Enzyme replacement therapy in Gaucher's disease: Large–Scale purification of glucocerebrosidase suitable for human administration" *Proc. Natl. Acad. Sci. USA* 74(8) 3560–3563.

Brady, R. O. (1966) "The Sphingolipidoses" *The New England Journal of Medicine*, 275(6):312–317.

B. M. Martin et al. "Glycosylation and Processing of High Levels of Active . . . " DNA 7(2) 99–106 (Mar. 1988).

M. Bergh et al. "Heterologers Expression at Human Glucocerebrosidase . . . " Absts. Paper. Am. Chem. Soc. 199th Meet. BIOT 51 (Apr. 1990).

M. Bergh et al. "Processing and Glycosylation of Human Glucocerebrosidase . . . " Absts. Papers. Am. Chem. Soc. 200th Meet. BIOT 109 (Aug. 1990).

G. J. Murray et al. "Lectin–Specific Targeting at Lysosomal Enzymes . . . " Meth. in Enzymol 149:25–42 (1987).

*Primary Examiner*—Robert A. Wax
*Assistant Examiner*—Rebecca Prouty
*Attorney, Agent, or Firm*—William G. Gosz

[57] ABSTRACT

A pharmaceutical composition comprising remodelled recombinant glucocerebrosidase (GCR) is described that provides a therapeutic effect at doses that are lower then those required using remodelled naturally occurring GCR. A method of treating patients with Gaucher's disease using remodelled recombinant GCR is also provided. In vivo uptake of exogenous molecules can be determined by extracting a mixture of cells from a subject, enriching the target cells in vitro, lysing the cells and determining the amount of exogenous molecules.

10 Claims, 2 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 498 amino acids
      ( B ) TYPE: amino acid
      ( C ) STRANDEDNESS:
      ( D ) TOPOLOGY: linear ( i i ) MOLECULE TYPE: protein ( x i ) SEQUENCE DESCRIPTION: SEQ ID NO:1:

```
Ala  Arg  Pro  Cys  Ile  Pro  Lys  Ser  Phe  Gly  Tyr  Ser  Ser  Val  Val  Cys
 1              5                     10                          15

Val  Cys  Asn  Ala  Thr  Tyr  Cys  Asp  Ser  Phe  Asp  Pro  Pro  Thr  Phe  Pro
              20                     25                      30

Ala  Leu  Gly  Thr  Phe  Ser  Arg  Tyr  Glu  Ser  Thr  Arg  Ser  Gly  Arg  Arg
              35                     40                      45

Met  Glu  Leu  Ser  Met  Gly  Pro  Ile  Gln  Ala  Asn  His  Thr  Gly  Thr  Gly
      50                    55                      60

Leu  Leu  Leu  Thr  Leu  Gln  Pro  Glu  Gln  Lys  Phe  Gln  Lys  Val  Lys  Gly
 65                   70                      75                          80

Phe  Gly  Gly  Ala  Met  Thr  Asp  Ala  Ala  Ala  Leu  Asn  Ile  Leu  Ala  Leu
              85                     90                      95

Ser  Pro  Pro  Ala  Gln  Asn  Leu  Leu  Leu  Lys  Ser  Tyr  Phe  Ser  Glu  Glu
              100                    105                     110

Gly  Ile  Gly  Tyr  Asn  Ile  Ile  Arg  Val  Pro  Met  Ala  Ser  Cys  Asp  Phe
              115                    120                     125

Ser  Ile  Arg  Thr  Tyr  Thr  Tyr  Ala  Asp  Thr  Pro  Asp  Asp  Phe  Gln  Leu
              130                    135                     140

His  Asn  Phe  Ser  Leu  Pro  Glu  Glu  Asp  Thr  Lys  Leu  Lys  Ile  Pro  Leu
 145                   150                     155                         160

Ile  His  Arg  Ala  Leu  Gln  Leu  Ala  Gln  Arg  Pro  Val  Ser  Leu  Leu  Ala
              165                    170                     175

Ser  Pro  Trp  Thr  Ser  Pro  Thr  Trp  Leu  Lys  Thr  Asn  Gly  Ala  Val  Asn
              180                    185                     190

Gly  Lys  Gly  Ser  Leu  Lys  Gly  Gln  Pro  Gly  Asp  Ile  Tyr  His  Gln  Thr
              195                    200                     205

Trp  Ala  Arg  Tyr  Phe  Val  Lys  Phe  Leu  Asp  Ala  Tyr  Ala  Glu  His  Lys
      210                    215                     220

Leu  Gln  Phe  Trp  Ala  Val  Thr  Ala  Glu  Asn  Glu  Pro  Ser  Ala  Gly  Leu
 225                   230                     235                         240

Leu  Ser  Gly  Tyr  Pro  Phe  Gln  Cys  Leu  Gly  Phe  Thr  Pro  Glu  His  Gln
              245                    250                     255

Arg  Asp  Phe  Ile  Ala  Arg  Asp  Leu  Gly  Pro  Thr  Leu  Ala  Asn  Ser  Thr
              260                    265                     270

His  His  Asn  Val  Arg  Leu  Leu  Met  Leu  Asp  Asp  Gln  Arg  Leu  Leu  Leu
              275                    280                     285

Pro  His  Trp  Ala  Lys  Val  Val  Leu  Thr  Asp  Pro  Glu  Ala  Ala  Lys  Tyr
      290                    295                     300

Val  His  Gly  Ile  Ala  Val  His  Trp  Tyr  Leu  Asp  Phe  Leu  Ala  Pro  Ala
 305                   310                     315                         320
```

-continued

| | | | | | | | | | | | | | | |
|---|---|---|---|---|---|---|---|---|---|---|---|---|---|---|
| Lys | Ala | Thr | Leu | Gly 325 | Glu | Thr | His | Arg | Leu 330 | Phe | Pro | Asn | Thr | Met 335 | Leu |
| Phe | Ala | Ser | Glu 340 | Ala | Cys | Val | Gly | Ser 345 | Lys | Phe | Trp | Glu | Gln 350 | Ser | Val |
| Arg | Leu | Gly 355 | Ser | Trp | Asp | Arg | Gly 360 | Met | Gln | Tyr | Ser | His 365 | Ser | Ile | Ile |
| Thr | Asn 370 | Leu | Leu | Tyr | His | Val 375 | Val | Gly | Trp | Thr | Asp 380 | Trp | Asn | Leu | Ala |
| Leu 385 | Asn | Pro | Glu | Gly | Gly 390 | Pro | Asn | Trp | Val | Arg 395 | Asn | Phe | Val | Asp | Ser 400 |
| Pro | Ile | Ile | Val | Asp 405 | Ile | Thr | Lys | Asp | Thr 410 | Phe | Tyr | Lys | Gln | Pro 415 | Met |
| Phe | Tyr | His | Leu 420 | Gly | His | Phe | Ser | Lys 425 | Phe | Ile | Pro | Glu | Gly 430 | Ser | Gln |
| Arg | Val | Gly 435 | Leu | Val | Ala | Ser | Gln 440 | Lys | Asn | Asp | Leu | Asp 445 | Ala | Val | Ala |
| Leu | Met 450 | His | Pro | Asp | Gly | Ser 455 | Ala | Val | Val | Val | Val 460 | Leu | Asn | Arg | Ser |
| Ser 465 | Lys | Asp | Val | Pro | Leu 470 | Thr | Ile | Lys | Asp | Pro 475 | Ala | Val | Gly | Phe | Leu 480 |
| Glu | Thr | Ile | Ser | Pro 485 | Gly | Tyr | Ser | Ile | His 490 | Thr | Tyr | Leu | Trp | His 495 | Arg |
| Gln | Arg | | | | | | | | | | | | | | |

ENHANCED IN VIVO UPTAKE OF GLUCOCEREBROSIDASE

CROSS REFERENCE TO RELATED APPLICATION

This application is a continuation-in-part of U.S. application Ser. No. 07/748,283, filed Aug. 21, 1991, now U.S. Pat. No. 5,236,838, a divisional application of U.S. application Ser. No. 455,507, filed Dec. 22, 1989, now abandoned, which was filed as a continuation-in-part of U.S. application Ser. No. 289,589, Dec. 23, 1988, now abandoned. The related applications are hereby incorporated by reference.

TECHNICAL FIELD

The present invention relates to the pharmacokinetics of proteins, in particular to glucocerebrosidase (GCR).

BACKGROUND

Gaucher's disease is an autosomal recessive lysosomal storage disorder characterized by a deficiency in the lysosomal enzyme, glucocerebrosidase (GCR). GCR hydrolyzes the glycolipid glucocerebroside that is formed after degradation of glucosphingolipids in the membranes of white blood cells and senescent red blood cells. In patients with Gaucher's disease, deficiency in this enzyme causes the glucocerebroside to accumulate in large quantities in the lysosomes of phagocytic cells located in the liver, spleen and bone marrow. Accumulation of these molecules causes a range of clinical manifestations including splenomegaly, hepatomegaly, skeletal disorder, thrombocytopenia and anemia.

Former treatments for patients suffering from this disease include administration of analgesics for relief of bone pain, blood and platelet transfusions and, in several cases, splenectomy. Joint replacements were sometimes necessary for patients who experienced bone erosion. In 1966, Brady published an article in The New England Journal of Medicine (vol. 275, p. 312) proposing enzyme replacement therapy with GCR as a treatment for Gaucher's disease. The current treatment of patients with Gaucher's disease relies on the administration of a carbohydrate remodelled GCR derived from the placenta, known as p-GCR. The carbohydrate remodelling converts the native molecule into a molecule that will bind to mannose receptors on phagocytic cells. While enzyme replacement therapy using remodelled p-GCR has been shown to be effective in treating patients, it is an expensive form of therapy and places a heavy economic burden on the health care system. The high cost of p-GCR results from the scarcity of the human placental tissue from which it is derived, a complex purification protocol, and the relatively large amounts of the therapeutic required for existing treatments. There is an urgent need to reduce the cost of GCR so that this life saving therapy can be provided to all who require it more affordably.

Unmodified glucocerebrosidase derived from natural sources is a glycoprotein with four carbohydrate chains. This protein does not target the phagocytic cells in the body and is therefore of limited therapeutic value. In developing the current therapy for Gaucher's disease, the terminal sugars on the carbohydrate chains of glucocerebrosidase are sequentially removed by treatment with three different glycosidases. This glycosidase treatment results in a glycoprotein whose terminal sugars consist of mannose residues. Since phagocytes have mannose receptors that recognize glycoproteins and glycopeptides with oligosaccharide chains that terminate in mannose residues, the carbohydrate remodeling of glucocerebrosidase has improved the targeting of the enzyme to these cells (Furbish et al., Biochem. Biophys. Acta 673:425, 1981)

This approach for improving the efficacy of glucocerebrosidase by remodelling the carbohydrate chains does not exclusively target glucocerebrosidase to phagocytes, such as Kupffer cells, in preference to other cells since other cells, such as sinusoid endothelial cells, have mannose receptors. These cells very likely compete with phagocytes for uptake of p-GCR by this receptor mediated pathway. In addition, there is considerable uptake of p-GCR by hepatocytes by a non-mannose receptor pathway(s). Uptake by non-phagocytic cells does not provide therapeutic value. As a result, p-GCR is administered in high doses, and the cost is considerable.

Until this time, the focus for achieving reduced cost for enzyme replacement therapy has been to obtain GCR from alternative sources to the placenta, the sources being either natural or synthetic (using recombinant DNA technology) (Sorge et al., P.N.A.S., 82:7289, 1985, and Tsuji et al., J. Biol. Chem., 261:50, 1986). However, at least as important is the ability to direct the enzyme more effectively to target cells using new methods for administration of the enzyme and novel compositions that favor improved pharmacokinetics. This approach has not previously been systematically investigated in vivo.

A means of determining how much modified GCR is delivered and taken up by target cells and non-target cells in the liver would be helpful in evaluating further modifications to the composition, formulation and administration of GCR and determining the cost benefit of these improvements for the patients. This involves a method for separating Kupffer cells from other non-parenchymal cells isolated from the liver. However, the isolation of specific cell types from an experimental animal can be technically complex using conventional techniques of separation that rely on size separation when different cell types are similar sized as found with Kupffer cells and endothelial cells in the liver. In these circumstances, it would be desirable to develop accurate and relatively simple methods to recover target cells such as Kupffer cells in order to measure uptake of exogenous GCR, and subsequently to determine the half life of the GCR at the site at which it acts in vivo.

For the foregoing reasons, new methods for treating patients with GCR that incorporate an understanding of the pharmacokinetics of the drug are required to provide treatments that are more cost effective than existing treatments for Gaucher's disease so as to provide life saving therapy to all who need it.

SUMMARY OF THE INVENTION

The present invention is directed to recombinant GCR having improved pharmacokinetics over naturally occurring GCR. In a preferred embodiment, the dose of a pharmaceutical composition comprising remodelled recombinant GCR is less then the dose of remodelled naturally occurring GCR providing a similar therapeutic effect. In a specific embodiment, the recombinant r-GCR has an amino acid sequence that differs from naturally occurring GCR by the presence of histidine in place of arginine at position 495. In another preferred embodiment, the carbohydrate remodelled r-GCR has increased fucose and N-acetyl glucosamine residues compared to remodelled naturally occurring GCR.

The invention also relates to a method of treating a human subject having Gaucher's disease by administration of the claimed GCR in an effective amount to achieve a therapeutic effect, the effective amount being dependent on the pharmacokinetics of the r-GCR where each dose of r-GCR being administered to the subject is less than the dose of naturally occurring GCR that would otherwise be administered in a similar manner to achieve the therapeutic effect.

Another embodiment of the invention relates to methods for determining the uptake of exogenous molecules in target cells in vivo. This procedure involves providing exogenous molecules, administering these molecules to an animal subject, extracting a mixture of cells from the subject, enriching the target cells in the mixture in vitro and quantifying the target cells; lysing the cells and determining the amount of exogenous molecules.

In another embodiment, a method to determine the uptake of exogenous GCR by Kupffer cells in vivo includes providing exogenous GCR, administering exogenous GCR to an animal subject, extracting cells of the liver from the subject, separating Kupffer cells away from other liver cells, quantifying the Kupffer cells, and lysing the Kupffer cells to determine the activity of exogenous GCR.

BRIEF DESCRIPTION OF THE DRAWINGS

The foregoing features of the invention will be more readily understood by reference to the following detailed description taken with the accompanying drawings in which.

DESCRIPTION OF SPECIFIC EMBODIMENTS

Figure 1:
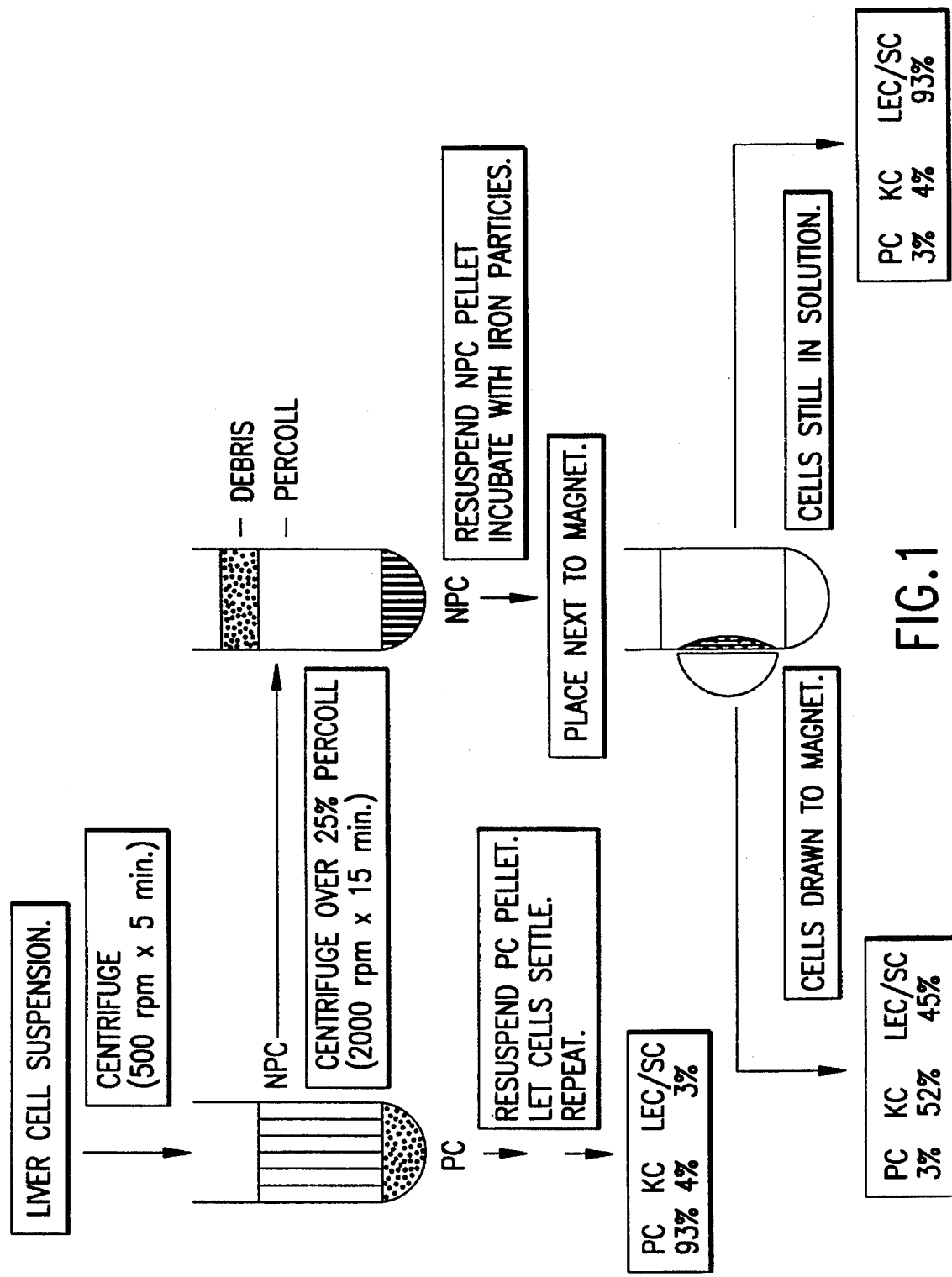
FIG. 1 is a graphical representation of the protocol for separating parenchymal cells, Kupffer cells and endothelial and stellate cells from a liver cell suspension.

The term "recombinant GCR" (r-GCR) as used in this description and in the following claims defines an enzymatically active glucocerebrosidase enzyme that has been obtained by cloning the genetic sequence for GCR and expressing this sequence in a eukaryotic cell culture thereby producing protein which is subsequently purified.

The term "pharmacokinetics" as used in this description and in the following claims describes the processing of GCR in vivo, which includes, for example, any of the steps of absorption into cells, distribution in vivo, metabolism and excretion.

The term "naturally occurring" as used in the description and in the following claims includes endogenous GCR or exogenous GCR, for example, that is derived from the placenta (p-GCR).

The term "remodelled" as used herein refers to the glycoprotein GCR that has been treated in such a way as to expose mannose residues on the appended oligosaccharide side chains. Remodelling may be performed by enzymatic reactions or by other means and may occur during the manufacturing process or as a result of additional steps after manufacturing has been completed.

The term "therapeutic effect" as used in the description and in the following claims is a significant alleviation of clinical symptoms of Gaucher's disease.

The term "exogenous molecule" as used in the description and in the following claims is here defined as a molecule originating outside the body.

A surprising and unexpected aspect of the present invention is the finding that r-GCR made according to the invention has improved pharmacokinetics compared with that of p-GCR and that the improved pharmacokinetics result at least in part from the improved affinity of the GCR for target cells compared with naturally occurring GCR.

These findings were made possible using a novel method of determining the efficacy of targeting that includes separating a single cell type from a mixture of cells that constitutes an organ. In the liver, both target cells (Kupffer cells) and non-target cells (endothelial cells) have receptors that recognize glycoproteins with mannose-terminating oligosaccharide chains. The improved uptake by Kupffer cells could not have been deduced in the absence of a method such as described and claimed here for determining the uptake of exogenous proteins by target cells in vivo.

Comparison of r-GCR with naturally occurring GCR

GCR derived from placenta (naturally occurring form) prepared for example, as described in Furbish et al. (1977) P.N.A.S. vol 74 pp 3560–3563 or from recombinant cells prepared, for example, as described in Example 1, can be treated with glycosidases so as to remodel the oligosaccharide structure on the surface of the protein and thereby improve the ability of GCR to target mannose receptors. The protocol for treatment of GCR with glycosidases follows standard protocols used to prepare commercially available remodelled p-GCR (Ceredase) (Furbish et al. 1981). The expectation was that following this carbohydrate remodelling step, both forms would have similar pharmacokinetics. Indeed, following the carbohydrate remodelling step, both forms show similar affinity for mannose receptors in "in vitro studies" using rat alveolar macrophages.

Figure 2:
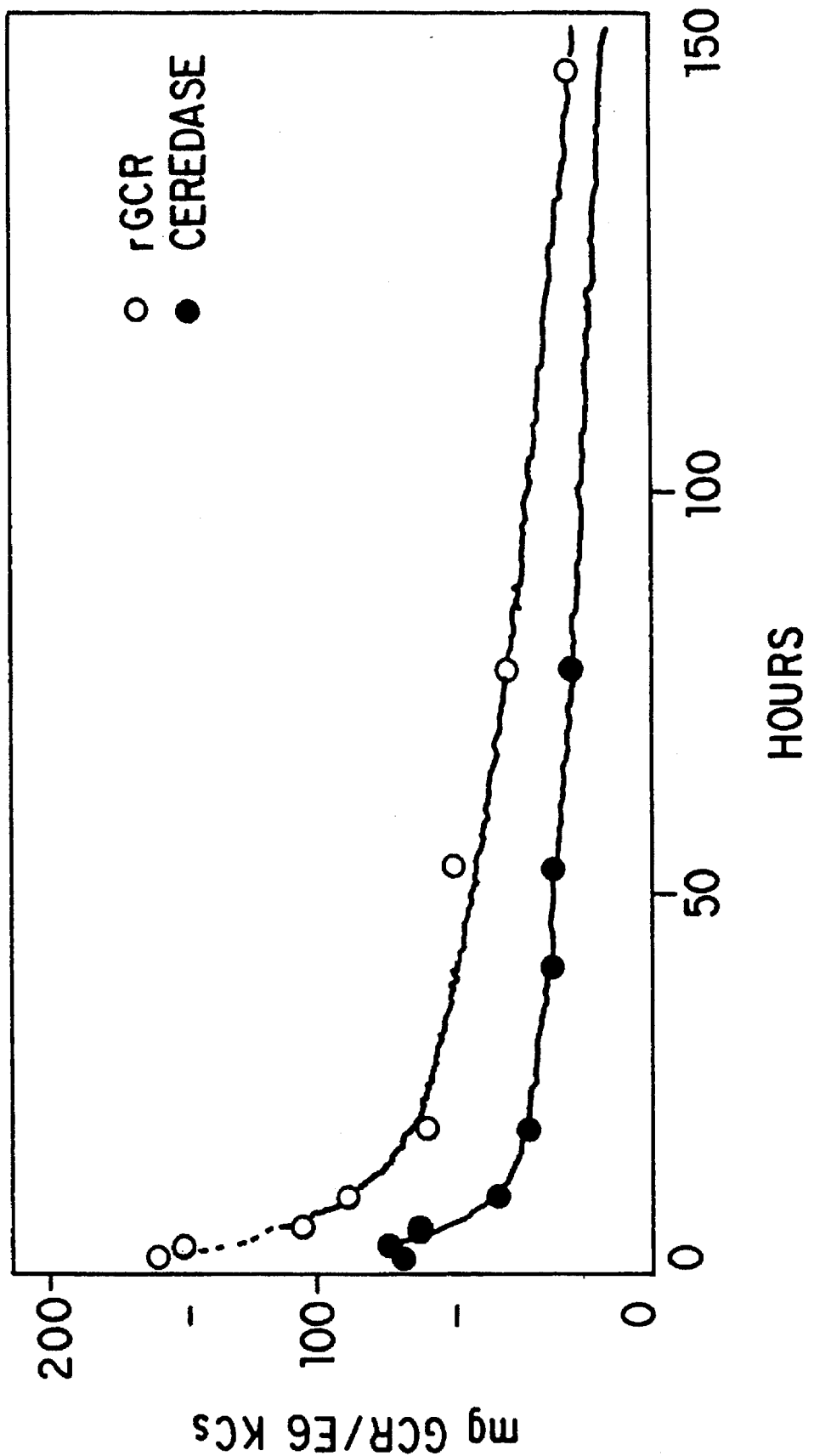
FIG. 2 is a graphical representation of the amount of exogenous GCR taken up by Kupffer cells in which exogenous GCR activity is plotted against time.

However, based on in vivo experiments described in Example 2, it was unexpectedly discovered (FIG. 2) that remodelled p-GCR and remodelled r-GCR have different cell type distributions in vivo although the blood clearance of both r-GCR and p-GCR is comparable. Approximately twice as much r-GCR targets Kupffer cells than does p-GCR. This difference was observed at every time point analyzed (FIG. 2). Table 1 shows that this effect is batch independent. Two batches of r-GCR (batch 1199 and batch 1167) were administered to mice according to the protocol in Example 2 and the animals sacrificed 0.33 hours after administration. The percentage of r-GCR retained in Kupffer cells was found to be twice that of p-GCR. This effect is also formulation independent. Table 1 shows that the mere formulation of p-GCR as r-GCR does not improve targeting to Kupffer cells.

The observed differences in pharmacokinetics may be due to differences in the chemical composition of r-GCR versus p-GCR. GCR is made up of 497 amino acid residues (Sorge et al 1985, Tsuji et al. 1986). According to a specific embodiment of the present invention, a single amino acid difference exists at position 495 between p-GCR and r-GCR where the arginine of p-GCR is replaced by a histidine. The substitution of histidine in place of arginine at position 495 appears to affect the structure of GCR. This affect has been demonstrated in differences in the sensitivity to digestion by trypsin and differences in the circular dichroism spectra of the two forms.

In addition to sequence differences, p-GCR and r-GCR have differences in carbohydrate structures that may contribute to differences in uptake by Kupffer cells. Following the remodelling, the carbohydrate moiety for r-GCR comprises 15–20% oligosaccharide having increased fucose and N-acetyl glucosamine residues compared to remodelled naturally occurring forms such as p-GCR. Prior to remodeling, the p-GCR has one high mannose chain plus three complex oligosaccharide chains. In contrast, all four of the carbohydrate chains on the r-GCR are complex. After carbohydrate remodeling, the majority of branches on the oligosaccharide chains of r-GCR and p-GCR terminate in mannose sugars. However, p-GCR retains one high mannose chain, which is absent in the r-GCR. The r-GCR has more fucose residues than the placental material, and more N-acetyl-glucosamine residues. In addition to altering the uptake of GCR by Kupffer cells via the mannose receptor, the differences in sugar composition and oligosaccharide structures may also effect uptake by other carbohydrate recognition systems on these cells and on other cell types in the body.

The consequence of small differences between the r-GCR and p-GCR amino acid and oligosaccharide composition appear to positively influence uptake by different cells of the liver, especially Kupffer cells. These differences may be explained by any of several models including: the reduction of uptake of r-GCR by non-target cells providing increased availability for target cells; increased affinity for other receptors on target cells in addition to mannose receptors; and increased affinity of binding with target cells.

The present invention will now be further illustrated by the following examples, which are not intended to be limiting in any way.

EXAMPLE 1

Production and Purification of r-GCR

R-GCR was produced by transfecting Chinese Hamster Ovary cells (CHO) with complementary DNA of GCR being incorporated into a bicistronic GCR-dhfr expression vector constructed from pSV2-dhfr (described in Subrami et al., Mol. and Cell. Biol., 9:854–86, 1981). The preparation of the vector containing the cloned coding sequence involved cutting pSV2-dhfr with Bgllll, blunt ending with T4 polymerase, recircularizing with T4 ligase, cutting again with Hindlll, blunt-ending, ligating to Bgllll linkers, cutting with Bgllll, ligating to recircularize, cutting with Bglll and ligating with a DNA fragment encoding GCR.

The GCR vector known as pGB20, was then transfected into CHO dihydrofolate reductase (DHFR) mutant cells DG44 (Urlaub et al., Som. Cell Molec. Genet. 12:555–666, 1986), and exponentially growing DG44 cells were transfected with 10 ug of plasmid pGB20 per 100 mm dish using the Lipofectin® transfection method as described by the manufacturer (BRL, Gaithersburg, Md.).

Following transfection, the medium was removed and replaced with a non-selective medium for 24 hours. This medium was replaced with a selective medium alpha-MEM (Gibco), minus nucleotides. Cell colonies grew in the selective medium were harvested and aliquots lysed with a 0.05M sodium citrate buffer, ph 6.2, containing 12.0 g/L sodium cholic acid and 12.0 ml/L of 1-butanol. The intracellular GCR levels were measured in the lysed samples using fluorogenic substrate 4-methyl umbelliferyl-b-D-glucoside (Suzuki, Methods in Enzymology, 50:478–479, 1978). After 12 days in selection media, cell colonies that secrete high levels of intracellular GCR were expanded and stepwise amplified with increasing levels of methotrexate up to 10 mM. Selected clones were then scaled up for r-GCR production based on secretion levels.

Purification of r-GCR

R-GCR secreted into the production media was purified by conventional purification techniques following a modification of the procedure described by Furbish et al. P.N.A.S., 74:3560, 1977. Substantially pure enzyme was then obtained following standard conventional purification techniques well known in the art. According to the preferred embodiment of the invention, the carbohydrate chains were remodelled during this purification process by sequential treatment with neuraminidase, galactosidase and β-N acetylglucosaminidase. R-GCR was then assayed for activity as described below. According to a preferred embodiment of the invention, routine amounts of r-GCR obtained were 1–10 mg/l. In alternative embodiments, remodelling may be accomplished by utilizing mutant cell lines deficient in certain carbohydrate synthetic pathways. Other methods of remodelling include chemical modification of the oligosaccharide of the purified recombinant GCR.

EXAMPLE 2

In Vivo Comparison of Uptake of r-GCR and p-GCR by Liver Cells

The sites of uptake of GCR was been determined for the mouse and it was found that 95% of the exogenous GCR is taken up by the liver with the remaining 5% being distributed throughout the other organs of the body. The liver of the mouse is composed of a mixture of cells that closely mimics the human liver in cell type and distribution. For example, the parenchymal cells are represented in a similar percentage to that present in human liver.

For the experiments summarized in Table 1, all mice were given a single bolus injection into the tail vein using 1 ug test substance per gm body weight and sacrificed 20 minutes after injection. Seven control animals were used to determine endogenous levels of GCR activity in the different cell types in the liver. These animals were treated in a similar manner to the experimental animals except that 1 μg mannosylated BSA per gm body weight was administered.

At different times after injection, the animal was anesthetized, the liver perfused with collagenase, the animal sacrificed and the liver excised. A suspension of liver cells was then prepared. This cell suspension contained about 65% hepatocytes (parenchymal cells) and about 35% non-parenchymal cells (Kupffer cells, endothelial cells and hepatocytes).

In order to determine the amount of uptake of GCR by Kupffer cells, it was first necessary to separate the different populations of cells. The procedure is schematically depicted in FIG. 1. The binucleate parenchymal cells of the liver could be readily sedimented by low speed centrifugation being relatively dense leaving Kupffer cells, endothelial cells and stellate cells in the supernatent. Kupffer cells were then separated from the endothelial and stellate cells using a novel magnetic separation technique in which latex coated iron particles were added to the cell suspension. The phagocytic Kupffer cells engulfed these particles and could be separated by a magnetic force applied to the side of the culture vessel. To further characterize the "magnetic" cells, the suspension of cells was placed on a spinning slide in a cytospin. Whereas small endothelial and stellate cells contained up to 2–3 magnetic particles associated with the membrane, the Kupffer cells incorporated as many as 10 or more iron particles that had been phagocytosed. The identity of the magnetic cells could be easily discerned by examining their morphology and esterase staining properties.

Morphologically, endothelial cells and stellate cells are small. In cytospins, the nuclei of these cells are spherical, centrally located and surrounded by a very small amount of cytoplasm. Plasma membranes of these cells appear smooth. These cells do not have napthal-AS-chloro esterase activity. In contrast, the Kupffer cells were identified by their size, their esterase activity and by their immunochemistry. Kupffer cells are much larger than endothelial cells. The Kupffer cell nuclei are crescent shaped, peripherally located and there is considerable amount of cytoplasm. Plasma membranes of these cells appear ruffled. Kupffer cells stained positively for esterase activity. The Kupffer cells were also positively identified by immunohistochemistry using mouse macrophage specific antibodies MCA 519 (Serotech, Kidlington, Oxon, UK) and BM8 (Biomedical Alternative International, Raleigh, N.C.). The amount of GCR was determined as a percentage of the total injected dose as shown in Table 1. Table 1 is a comparison of the distribution of r-GCR formulated in 50 mM citrate buffer pH 5.6 containing 3% mannitol and 0.01% Tween 80 in different cell types, the values given being % injected dose. P-GCR was formulated as a liquid in 1% HSA, 50 mM citrate buffer, pH 5.9. Only 7.3% of p-GCR targeted to Kupffer cells whereas for r-GCR, 15.3% of the injected dose of lot #1199 targeted to Kupffer cells and 14.2% of the injected dose of lot #1167 targeted to Kupffer cells. The two different lots of r-GCR behaved very similarly. Furthermore, preparing p-GCR in the same formulation as r-GCR did not improve targeting to Kupffer cells.

The observation that r-GCR targets Kupffer cells better than does p-GCR was initially made using animals sacrificed at a single time point (20 minutes) after injection of control or test substance (see Table 1). This is consistent with the results obtained from animals sacrificed at longer time points following injection. In the experiments summarized in FIG. 2, animals were sacrificed at either 20 minutes, or 2, 4, 8, 12, 15, 36, 72, or 144 hours after injection of either r-GCR or p-GCR. The amount of exogenous GCR in Kupffer cells was determined by lysing cells and using standard assays for measuring GCR activity. In a specific embodiment, the specific activity of GCR was determined in three different fractions of liver cells.

The first fraction was the pelleted material from the initial slow speed centrifugation step. This fraction contained most of the parenchymal cells (PC). The second fraction consisted of cells that were drawn to a magnet following incubation with latex coated iron particles. This fraction contained slightly more Kupffer cells than endothelial cells and stellate cells, and contained very few parenchymal cells. The third fraction consisted of cells that were not drawn to a magnet following incubation with iron particles. The majority of these cells were the smaller liver endothelial cells and stellate cells. The average cell type composition of each fraction is noted in FIG. 1. The GCR activity in each fraction was expressed algebraically as the sum of the contribution of GCR activity of each of the three cell types in that fraction. Since there were only three unknowns, three simultaneous equations could be derived, and the unknowns could be resolved for the amount of GCR activity in each cell type. This GCR activity represented the sum of endogenous and exogenous activity. Endogenous activities in each cell type were determined from control animals. The amount of exogenous GCR taken up by each cell type was then determined by subtracting out endogenous GCR activity from the total GCR activity. At every time point, more r-GCR than p-GCR was calculated to be in the Kupffer cells of the liver. These data confirm that the uptake of r-GCR by Kupffer cells was significantly greater then with p-GCR.

Taken together, It was deduced from these data that the cell type distribution properties of r-GCR was significantly different from those of p-GCR. The different behaviors of these molecules were unexpected, and would not have been noted without the novel method of the present invention for rapidly separating liver cells into three distinct populations that has been described in this text. The results showed that any differences in formulation could not account for the differences in the behavior of r-GCR from that of p-GCR. Instead, it was concluded that differences in targeting must be due to differences in the structure of r-GCR molecule and the p-GCR molecule. These differences could be found in the amino acid structure and carbohydrate compositions outlined above.

Although certain preferred embodiments of the present invention have been described, the spirit and scope of the invention is by no means restricted to what is described above.

TABLE 1

COMPARISON OF CELL TYPE DISTRIBUTION OF
r-GCR, p-GCR (CEREDASE ® ) AND p-GCR FORMULATED AS r-GCR
DATA ANALYZED AS % INJECTED DOSE
(Mice were sacrificed 0.33 hrs. after injection of test substances)

| TEST SUBSTANCE | LECs/SCs (% injected dose) | KCs (% injected dose) | PCs (% injected dose) | TOTAL (% injected dose) |
|---|---|---|---|---|
| r-GCR (1199) | −1.3 | 19.1 | 58.3 | 76.1 |
|  | −7.3 | 18.5 | 41.0 | 52.3 |
|  | 2.7 | 12.0 | 54.9 | 69.6 |
|  | 6.5 | 11.5 | 53.3 | 71.3 |
| Mean ± SD: | 0.15 ± 5.9 | 15.3 ± 4.1 | 51.7 ± 7.5 | 67.3 ± 10.4 |
| r-GCR (1167) | 5.4 | 11.0 | 55.9 | 72.3 |
|  | 2.7 | 17.8 | 39.8 | 60.3 |
|  | 4.4 | 12.1 | 58.5 | 75.0 |
|  | 2.1 | 15.7 | 35.8 | 53.6 |
| Mean ± SD: | 3.7 ± 1.5 | 14.2 ± 3.2 | 47.5 ± 11.4 | 65.3 ± 10.1 |
| remodeled | 6.9 | 9.1 | 68.5 | 84.6 |
| p-GCR | 14.9 | 7.0 | 55.9 | 77.8 |
|  | 13.6 | 5.8 | 55.7 | 75.2 |
| Mean ± SD: | 11.8 ± 4.3 | 7.3 ± 1.7 | 60.0 ± 7.3 | 79.2 ± 4.9 |
| remodeled | 16.1 | 6.8 | 56.9 | 79.8 |
| p-GCR | 12.8 | 7.6 | 59.2 | 79.6 |
| (using r-GCR | 0.3 | 9.0 | 56.2 | 65.4 |
| formulation) | 0.4 | 11.3 | 43.4 | 55.2 |
| Mean ± SD: | 7.3 ± 8.3 | 8.6 ± 2.0 | 53.9 ± 7.1 | 69.9 ± 12.0 |

What is claimed is:

1. A pharmaceutical composition, comprising:
   remodeled recombinant GCR, obtained from CHO cells, wherein the remodeled recombinant GCR has exposed mannose terminal residues on appended oligosaccharides, in an effective dosage suitable for significantly alleviating clinical symptoms of Gaucher's disease, such that the dose is substantially less than the effective dose using remodeled naturally occurring GCR.

2. The pharmaceutical composition of claim 1, wherein the recombinant GCR differs from naturally occurring GCR by having a histidine at amino acid number 495.

3. The pharmaceutical composition of claim 1, wherein the remodelled recombinant GCR has increased fucose compared to remodelled naturally occurring GCR.

4. The pharmaceutical composition of claim 1 wherein the remodelled recombinant GCR has increased N-acetyl glucosamine residues compared to remodelled naturally occurring GCR.

5. A method for treating a human subject having Gaucher's disease using exogenous GCR, comprising:
   (a) providing a recombinant form of GCR obtained from CHO cells and capable of effectively targeting cells abnormally deficient in GCR, wherein the recombinant GCR has exposed terminal mannose residues on appended oligosaccharides;
   (b) administering such form of the GCR to the subject in doses sufficient to achieve a therapeutic effect, each dose being dependent on the effective targeting of cells abnormally deficient in GCR; and each dose of such form of GCR being substantially less than the dose of naturally occurring GCR that would otherwise be administered in a similar manner to achieve the therapeutic effect.

6. A method according to claim 5, wherein the recombinant GCR differs from naturally occurring GCR by having a histidine at amino acid number 495.

7. A method according to claim 5, wherein the recombinant GCR has a carbohydrate moiety having increased fucose and N-acetylglucosamine residues compared to the naturally occurring forms of GCR.

8. A method according to claim 5, wherein the targeting capability in step (a) is determined in relation to the uptake by a population of target cells and the recombinant GCR has increased affinity for the target cells in comparison with that of naturally occurring GCR.

9. A method according to claim 8, wherein the cells at the target site are Kupffer cells in the liver.

10. A pharmaceutical composition for significantly alleviating clinical symptoms of Gaucher's disease comprising remodeled recombinant GCR obtained from CHO cells the remodeled recombinant GCR having an effective dosage that is substantially less than the effective dosage for remodeled naturally occurring GCR.

\* \* \* \* \*

UNITED STATES PATENT AND TRADEMARK OFFICE
CERTIFICATE OF CORRECTION

PATENT NO. : 5,549,892

DATED : August 27, 1996

INVENTOR(S) : BethAnn Friedman and Michael Hayes

It is certified that error appears in the above-indentified patent and that said Letters Patent is hereby corrected as shown below:

ON THE TITLE PAGE:

In the Attorney, Agent of Firm section, please delete "William S. Gosz" and insert --Harriet M. Strimpel, Bromberg & Sunstein LLP--

Signed and Sealed this

Second Day of September, 1997

*Attest:*

BRUCE LEHMAN

*Attesting Officer*  Commissioner of Patents and Trademarks